United States Patent
Justa et al.

(10) Patent No.: US 11,337,907 B2
(45) Date of Patent: May 24, 2022

(54) HAIR-DYEING COMPOSITION FOR MINIMIZING AMMONIUM HYDROXIDE CONTENT AND ODOR AND METHOD OF PRODUCING THE SAME

(71) Applicant: COTY INC., New York, NY (US)

(72) Inventors: Sergio Ricardo Justa, São Paulo (BR); Simone Aparecida da França Stefoni, São Paulo (BR); Jéssica Francischini Novais, São Paulo (BR); Beatriz de Moura Abreu, Cajamar (BR)

(73) Assignee: Wella Operations US, LLC, Calabasas, CA (US)

( * ) Notice: Subject to any disclaimer, the term of this patent is extended or adjusted under 35 U.S.C. 154(b) by 0 days.

(21) Appl. No.: 17/258,436

(22) PCT Filed: Jul. 2, 2019

(86) PCT No.: PCT/US2019/040375
§ 371 (c)(1),
(2) Date: Jan. 6, 2021

(87) PCT Pub. No.: WO2020/010128
PCT Pub. Date: Jan. 9, 2020

(65) Prior Publication Data
US 2021/0267860 A1    Sep. 2, 2021

Related U.S. Application Data

(60) Provisional application No. 62/694,515, filed on Jul. 6, 2018.

(51) Int. Cl.
*A61Q 5/10* (2006.01)
*A61K 8/41* (2006.01)
*A61K 8/34* (2006.01)
(Continued)

(52) U.S. Cl.
CPC .............. *A61K 8/415* (2013.01); *A61K 8/342* (2013.01); *A61K 8/347* (2013.01); *A61K 8/361* (2013.01);
(Continued)

(58) Field of Classification Search
CPC . A61Q 5/10; A61K 8/22; A61K 8/411; A61K 8/415; A61K 8/41; A61K 8/342;
(Continued)

(56) References Cited

U.S. PATENT DOCUMENTS 5,021,066 A    6/1991 Aeby et al.
5,102,655 A    4/1992 Yoshihara et al.
(Continued)

FOREIGN PATENT DOCUMENTS

WO    WO 2016016148 A1 *    2/2016    ............... A61Q 5/10

OTHER PUBLICATIONS

"Personal Care Product List—Switzerland" Univar Personal Care (2014); p. 15.
International Search Report issued in connection with PCT Application No. PCT/US2019/040375 dated Sep. 23, 2019.

*Primary Examiner* — Eisa B Elhilo
(74) *Attorney, Agent, or Firm* — Victoria Friedman; Dennemeyer & Associates, LLC

(57) ABSTRACT

A hair-dyeing composition with an effect of minimizing hair damage and scalp irritation caused by ammonia prescription and ammonia odor, which is capable of decreasing ammonia odor peculiar to a hair-dyeing composition and also of supplementing the hair with amino acids similar to hair proteins to decrease hair damage, especially hair roughness and hair shortening, for healthy dyeing and a method of producing the same.

9 Claims, 2 Drawing Sheets

(51) Int. Cl.
    *A61K 8/36*     (2006.01)
    *A61K 8/37*     (2006.01)
    *A61K 8/39*     (2006.01)
    *A61K 8/46*     (2006.01)
    *A61K 8/55*     (2006.01)

(52) U.S. Cl.
    CPC ............... *A61K 8/375* (2013.01); *A61K 8/39* (2013.01); *A61K 8/41* (2013.01); *A61K 8/411* (2013.01); *A61K 8/463* (2013.01); *A61K 8/55* (2013.01); *A61Q 5/10* (2013.01)

(58) Field of Classification Search
    CPC .......... A61K 8/347; A61K 8/39; A61K 8/375; A61K 8/361; A61K 8/676; A61K 2800/522; A61K 8/463
    USPC ............................................................ 8/405
    See application file for complete search history.

(56) References Cited

U.S. PATENT DOCUMENTS

| | | |
|---|---|---|
| 6,835,018 B2 | 12/2004 | Miczewski et al. |
| 2004/0098816 A1* | 5/2004 | Au ............ A61K 8/22 8/405 |
| 2007/0174976 A1* | 8/2007 | Au ............ A61K 8/19 8/405 |
| 2010/0242187 A1 | 9/2010 | Miyabe |
| 2014/0338135 A1 | 11/2014 | Kim et al. |
| 2015/0209250 A1* | 7/2015 | Massoni ............ A61Q 5/10 8/406 |
| 2016/0175233 A1* | 6/2016 | Benn ............ A61Q 5/10 8/401 |
| 2017/0216174 A1* | 8/2017 | Aeby ............ A61K 8/55 |
| 2018/0021600 A1 | 1/2018 | Kobayshi et al. |

* cited by examiner

HAIR-DYEING COMPOSITION FOR MINIMIZING AMMONIUM HYDROXIDE CONTENT AND ODOR AND METHOD OF PRODUCING THE SAME

CLAIM FOR PRIORITY

This patent application claims the benefit of priority to U.S. Provisional Application Ser. No. 62/694,515, filed Jul. 6, 2018, and titled "HAIR-DYEING COMPOSITION FOR MINIMIZING AMMONIUM HYDROXIDE CONTENT AND AMMONIUM HYDROXIDE ODOR AND METHOD OF PRODUCING THE SAME" which is incorporated by reference herein in its entirety.

FIELD

The present invention relates to a hair-dyeing composition having the objective to minimize hair damage and scalp irritation caused by ammonium hydroxide and its characteristic malodor, in a composition. Particularly, the hair-dyeing composition of the present invention is capable of providing a color coverage to the hair, equivalent to an ammonium hydroxide composition, without the malodor or harm to the scalp, for a healthy dyeing process to the consumer and to the hair-dyeing practitioner, such as a hairdresser.

BACKGROUND

Description of the Related Art

Generally, oxidized permanent hair dyeing compositions can be used for covering a gray hair, styling a gray hair. Most of them consist of an ammonium hydroxide solution based dyeing agent and an oxidation agent that are mixed immediately before use. The dyeing agent usually includes a diamine-based oxidation dye, an ammonium hydroxide solution, a monoethanolamine and an ammonium thioglycolate. The oxidation agent usually includes an oxidation active such as a hydrogen peroxide.

The components that are the essential ingredients of the hair dyeing composition are also the causative materials of hair damage (hair loss, hair cutting, hair cracking), and also offenders to the scalp (erythema, swelling, itching, stinging, rash and the like), and a characteristic smell.

The ammonium hydroxide solution, which is used as an alkaline agent, serves to swell and softens the hair, so that the dye can easily penetrate the hair, increasing the durability of the hair dyeing. However, due to its toxicity and strong volatility, it is also a substance also capable of causing damage to respiratory organs and seborrheic dermatitis.

SUMMARY

Inventive embodiments disclosed herein have been made in an effort to solve the problems of the conceptual description of the conventional art as described above, and the objective of the present invention is to provide a hair-dyeing composition with an effect of minimizing hair damage and scalp irritation caused by ammonium hydroxide prescription and its characteristic malodor. The present invention uses decreasing contents, or even no content at all of ammonium hydroxide whilst also providing a hair-dyeing composition.

Inventive embodiments provide a hair-dyeing composition which is particularly capable of providing color coverage to the hair, equivalent to an ammonium hydroxide composition, without the malodor or harm to the scalp. The art relates to alternatives to ammonium hydroxide, such as monoethanolamine. However, as it delivers poor color coverage, i.e. around 50%, or less, such alternative agent is routinely combined with ammonium hydroxide, resulting again in undesired malodor and affliction to the scalp.

According to an aspect of the inventive embodiments to achieve the objects described above, there is provided a hair-dyeing composition including: a dyeing agent and an oxidizing agent. The dyeing agent having an amino propanol alkalinizing agent, such as 2-Dimethylamino-2-methylpropanol, aminomethyl propanol or dimethylamino methylpropanol. Preferably, the oxidizing agent is present from about 0.5 to about 7 percent by weight, based on the total weight of the dyeing agent.

In one embodiment, the dyeing agent further contains an antioxidant, from about 0.1 to about 5 percent, based on the total weight of the dyeing agent; a reducing agent from about 0.1 to about 5 percent, a base and a coupling from about 0.01 to about 5 percent. Preferably, the dyeing agent also contains a hair conditioner, from about 2 to about 6 percent, based on the total weight of the dyeing agent; more preferably, a Peg-2 Dimeadowfoamamidoethylmonium Methosulfate, lauryl alcohol or a mixture thereof.

An emollient agent is also present, preferably selected from the group cetearyl alcohol, dicaprylyl ether, glyceryl stearate, oleic acid, oleyl alcohol, pentaerythrityl tetraisostearate and its mixtures; in an amount ranging from about 4 to about 50 percent by weight, based on the total weight of the dyeing agent.

The oxidizing agent having an oxidation active, preferably a hydrogen peroxide, from about 1 to about 20 percent by weight based on the total weight of the oxidizing agent; an emollient from about 1 to about 10 percent; an emulsifying agent from about 0.01 to about 5 percent by weight based on the total weight of the oxidizing agent and a solvent as the remainder.

For some embodiments, for better performance and color coverage, the hair-dyeing composition has a mixing ratio of about 1:1 to about 1:3 of alkalizing agent to the oxidizing agent, as a weight ratio.

For some embodiments, the hair-dyeing composition is substantially free of ammonium hydroxide. The term "substantially free of" means that the ammonium hydroxide that the hair-dyeing composition is substantially free, is present in an amount of less than about 10 percent, less than about 9 percent, less than about 8 percent, less than about 7 percent, less than about 6 percent, less than about 5 percent, less than about 4 percent, less than about 3 percent, less than about 2 percent or less than about 1 percent, in weight, of the hair-dyeing composition.

BRIEF DESCRIPTION OF THE DRAWINGS

The above features and advantages of the present invention will be more apparent from the following detailed description taken in conjunction with the accompanying figures, in which.

DETAILED DESCRIPTION

Hereinafter, preferred embodiments of the invention will be described in more detail with reference to the accompanying drawings.

The hair-dyeing composition according to one embodiment of the present invention contains a dyeing gent; and an oxidizing agent, wherein the dyeing agent having an alkalizing agent selected from the group of 2-Dimethylamino-2-methylpropanol, aminomethyl propanol and dimethylamino methylpropanol, or its mixtures, from about 0.5 to about 7 percent by weight based on the total weight of the dyeing agent; an antioxidant from about 0.1 to about 5 percent; a reducing agent from about 0.1 to about 5 percent by weight; a base and a coupling from about 0.01 to about 5 percent by weight; and a solvent as the remainder. The oxidizing agent having a hydrogen peroxide from about 1 to about 20 percent by weight based on the total weight of the oxidizing agent; an emollient from about 1 to about 10 percent by weight; an emulsifying agent from about 0.01 to about 5 percent by weight based on the total weight of the oxidizing agent and a solvent as the remainder.

The present inventors have studied compositions that are capable of decreasing the irritating odor, especially the ammonia odor, generated when using an oxidative hair-dyeing composition and confirmed that using an amino propanol as an alkalizing agent, such as a dimethylamino methylpropanol, instead of ammonium hydroxide as the main alkalizer, the composition is capable of achieving achieve excellent color coverage while having diminute amounts of ammonium hydroxide and, consequently, without the malodor of ammonium hydroxide and its harmful effects to the scalp. As a result of studies on various compositions, the present inventors have confirmed that the ammonium hydroxide is decreased when the alkalizing agent, preferably a dimethylamino methylpropanol, is used and excellent hair color coverage is achieved, which is equivalent to an alkalinizing agent ammonium hydroxide, thereby completing the present invention.

In detail, a composition using an alkalizing agent such as ammonium hydroxide provides good alkalization, delivers good color coverage but mostly undesired malodor and damage to the scalp and hair. In view of the good color coverage, the alkalizing agent of conventional hair-dyeing compositions is ammonium hydroxide, which volatilizes and causes an irritating odor and adversely affect the bodies of the practitioner and the customer during the procedure of dyeing.

Accordingly, it is a general desire to achieve good color coverage whilst preventing the malodor, and various reducing agents have been researched. As a result, it has been confirmed that the substituting varying amounts of the ammonium hydroxide for an amino propanol prevented the hair-dyeing composition to have the characteristic malodor whilst achieving equivalent results of color coverage.

Figure 1:
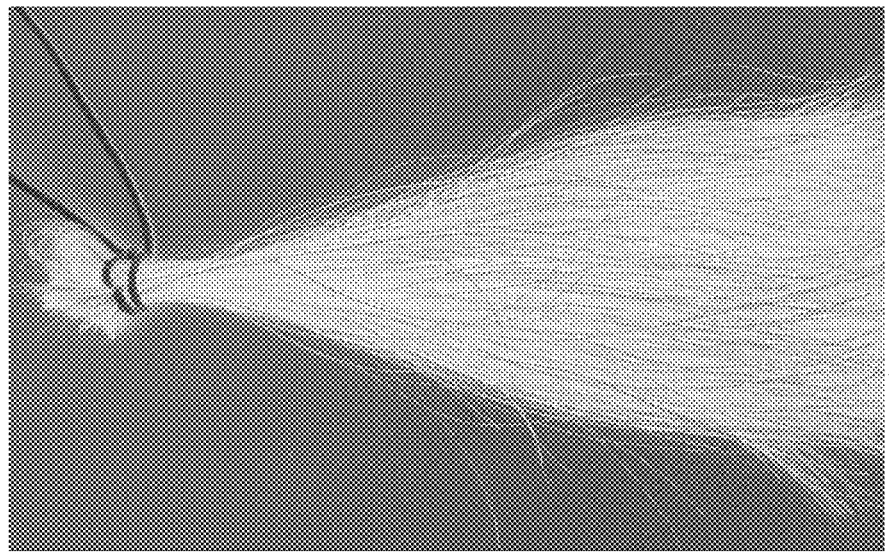
FIG. 1 is a black and white negative photograph, illustrating an untreated natural hair tress having 30% of gray hair.
Figure 2:
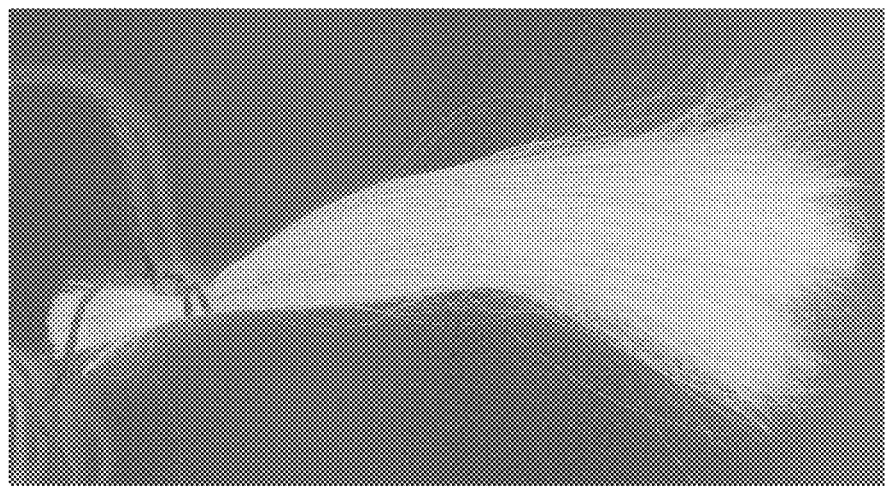
FIG. 2 is a black and white negative photograph illustrating a hair tress having 30% of gray hair treated with the composition of present invention.
Figure 3:
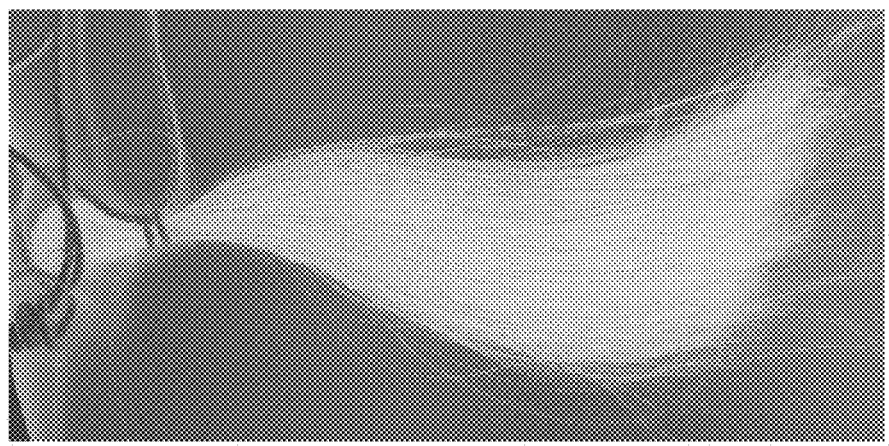
FIG. 3 is a black and white negative photograph illustrating a hair tress having 30% of gray hair treated with an ammonium hydroxide composition as a Comparative Formulation.

It has been confirmed that an alkalizing agent as an amino propanol, preferably selected from the group of 2-Dimethylamino-2-methylpropanol, aminomethyl propanol and dimethylamino methylpropanol, or its mixtures, from about 0.5 to about 7 percent by weight based on the total weight of the dyeing agent, are suitable as an alkalizing agent that delivers good color coverage. FIG. 1 is a black and white negative photograph illustrating an untreated, natural hair tress having 30% of gray hair. FIG. 2 is a black and white negative photograph illustrating a hair tress having 30% of gray hair treated with a composition of the present invention. FIG. 3 is a black and white negative photograph illustrating a hair tress having 30% of gray hair treated with an ammonium hydroxide composition as a Comparative Formulation. Comparison by visual inspection of the hair tress treated with the hair-dyeing composition of the present invention (FIG. 2) with the hair tress treated with an ammonium hydroxide composition (FIG. 3) illustrates the similar color coverage of both compositions. The present invention delivers equivalent color coverage of an ammonium hydroxide-based composition, without its drawbacks, such as malodor and scalp irritation and health issues.

To complete de hair-dyeing composition, the dyeing agent may contain an emulsifying agent, preferably selected from Ceteareth-20, dicetyl phosphate, Laureth-8, lauryl alcohol, oleic acid or its mixtures. It may further contain an emulsifying agent in an amount of from about 0.01 to about 5 percent by weight based on the total weight of the dyeing agent.

The base and coupling in the dyeing agent may be selected from the group consisting of phenylenediamine, such as toluene-2,5-diamine sulfate, 2,4-diaminophenoxyethanol hydrochloride, aminophenols, such as m-aminophenol, naphtols, pirazolones, resorcinol, and a mixture thereof, but these are exemplary of the present invention, and the invention is not intended to be limited thereto. The base and coupling are preferably contained in an amount of from about 0.01 to about 5 percent by weight based on the total weight of the dyeing agent, but when the content is out of the above range, there may be a problem that proper color development is not achieved.

The dyeing agent may further contain a hair conditioning from about 2 to about 6 percent by weight based on the total weight of the dyeing agent, and the hair conditioning may be Peg-2 Dimeadowfoamamidoethylmonium Methosulfate, lauryl alcohol or a mixture thereof.

In the dyeing agent, the solvent may be water. Alternatively, the solvent may be ethanol, laureth, glycerin.

The dyeing agent may further contain from about 4 to about 50 percent by weight of an emollient agent selected from the group cetearyl alcohol, dicaprylyl ether, glyceryl stearate, oleic acid, oleyl alcohol, pentaerythrityl tetraisostearate, and mixtures thereof. The solvent of the oxidizing agent may be the same and/or similar to the solvent of the dyeing agent.

The oxidizing agent is an oxidizing active hydrogen peroxide, preferably from about 1 to about 20 percent by weight based on the total weight of the oxidizing agent. The emollient of the oxidizing agent is preferably from about 1 to about 10 percent and an emulsifying agent is also desired, from about 0.01 to about 5 percent by weight based on the total weight of the oxidizing agent.

The dyeing agent, the oxidizing agent, or both, may further contain a first additive selected from the group consisting of an antioxidant, a sequestering agent, a perfume, and a mixture thereof. The dyeing agent, the oxidizing agent, or both, may further contain a second additive selected from the group consisting of a hair softening agent, a conditioning agent, a hair polishing agent, and a mixture thereof. They may further contain a third additive selected from the group consisting of a sequestering agent, a perfume, and a mixture thereof.

The above-mentioned first to third additives may be commercially purchased by those skilled in the field of hairstyling, particularly in the hair-dyeing composition manufacturing field and contained in the composition in an appropriate amount to control the physical properties of the hair-dyeing composition and to improve the stability and the like of the product.

Hereinafter, composition ranges for some embodiments are described at Table 1 and are illustrative of the present invention and should not be construed as limiting the scope of the invention.

TABLE 1

| Ingredient | Range |
| --- | --- |
| 2,4-Diaminophenoxyethanol Hcl | 0.01-1 |
| 2-methyl-2-(methylamino)-1-propanol | 0.01-1 |
| Alcohol | 0-20 |
| Aminomethyl Propanol | 0.001-0.02 |
| Aqua | 25-90 |
| Ceteareth-20 | 0-1 |
| Cetearyl Alcohol | 0-1 |
| Ceteth-10 Phosphate | 0-1 |
| Dicetyl Phosphate | 0-1 |
| Dimethylamino Methylpropanol | 0.5-7 |
| Glyceryl Stearate | 0-4 |
| Glycerin | 0-7 |
| Glyceryl Stearate | 0-4 |
| M-Aminophenol | 0.01-1 |
| Laureth-8 | 0-40 |
| Oleic Acid | 1-15 |
| P-Aminophenol | 0-0.5 |
| Parfum | 0.1-1.5 |
| Pentaerythrityl Tetraisostearate | 0-1.5 |
| Polyquatemium-22 | 0-5 |
| P-Phenylenediamine | 0.1-1.3 |
| Resorcinol | 0.1-1 |
| Sodium Erythorbate | 0-0.5 |
| Sodium hydrossulfite | 0-0.15 |
| Styrene/VP Copolymer | 0-0.15 |
| Tetrasodium EDTA | 0-0.5 |

From the ranges of Table 1, an Example Formulation was prepared with 5.7 percent of Dimethylamino Methylpropanol, 0.06 percent of 2-methyl-2-(methylamino)-1-propanol and 0.0060 percent of Aminomethyl Propanol. A Comparative Formulation was prepared with a similar composition but having 3.6 percent of ammonium hydroxide instead of the amino propanol alkalinizing agent used in the Example Formulation. Comparing images from FIGS. 1-3 confirms that the hair-dyeing composition of the Example formulation, according to the present invention, exhibits remarkably equivalent dyeing property and color coverage to the Comparative Formulation. The Example Formulation and Comparative Formulation were applied to the hair tresses with an oxidizing agent having 9 percent of hydrogen peroxide.

According to inventive embodiments disclosed herein, it is possible to provide a hair-dyeing composition which is capable of decreasing ammonia odor generated during hair dyeing, especially during hair dyeing using an oxidative hair-dyeing composition, without enhancing or deteriorating the dyeing power and at the same time decreasing damage of the hair and harmfulness to the human body of the hair-dyeing practitioner, such as a hairdresser and the customer.

While inventive embodiments have been described with respect to the specific embodiments, it will be apparent to those skilled in the art that various changes and modifications may be made without departing from the spirit and scope of the invention as defined in the following claims.

What is claimed is:

1. A hair-dyeing composition comprising:
a dyeing agent; and
an oxidizing agent, wherein:
the dyeing agent is a combination of components consisting of:
an alkalizing agent, wherein said alkalizing agent is selected from the group consisting of 2-dimethylamino-2-methylpropanol, aminomethyl propanol and dimethylamino methylpropanol or its mixtures, from about 0.5 to about 7 percent by weight based on the total weight of the dyeing agent;
an antioxidant from about 0.1 to about 5 percent by weight, based on the total weight of the dyeing agent;
a reducing agent from about 0.1 to about 5 percent by weight, based on the total weight of the dyeing agent; and,
a base and coupler from about 0.01 to about 5 percent by weight, based on the total weight of the dyeing agent; a hair conditioning agent; an emulsifying agent; an emollient agent and ammonium hydroxide;
the oxidizing agent comprises a hydrogen peroxide from 1 to 20 percent by weight, based on the total weight of the oxidizing agent; and,
the hair-dyeing composition is free of ethanolamine.

2. The hair dyeing composition of claim 1, wherein the base and coupler are selected from the group consisting of phenylenediamines, 2,4diaminophenoxyethanol hydrochloride, aminophenols, naphtols, pirazolones, resorcinol, or a mixture thereof.

3. The hair dyeing composition of claim 1, wherein the hair conditioning agent presents in the amount of 2 to 6 percent by wt., based on the total weight of the dyeing agent and wherein the hair conditioning agent is selected from the group consisting of Peg-2 Dimeadowfoamamidoethylammonium Methosulfate, lauryl alcohol or a mixture thereof.

4. The hair dyeing composition of claim 1, wherein the emulsifying agent is selected from the group consisting of Ceteareth-20, dicetyl phosphate, Laureth-8, lauryl alcohol and oleic acid.

5. The hair dyeing composition of claim 1, wherein the emollient agent is selected from the group consisting of cetearyl alcohol, dicaprylyl ether, glyceryl stearate, oleic acid, oleyl alcohol, pentaerythrityl tetraisostearate, or its mixture, from about 4 to about 50 percent by weight, based on the total weight of the dyeing agent.

6. The hair dyeing composition of claim 1, wherein the oxidizing agent further comprising an emollient from about 1 to 10 percent by weight, based on the total weight of the oxidizing agent and an emulsifying agent from about 0.01 to about 5 percent by weight, based on the total weight of the oxidizing agent.

7. The hair-dyeing composition of claim 1 wherein the composition has a mixing ratio of about 1:1 to about 1:3 of alkalizing agent to the oxidizing agent, as a weight ratio.

8. The hair dyeing composition of claim 1, wherein ammonium hydroxide presents at a concentration of less than about 1 percent by weight, based on the total weight of the dyeing agent.

9. A hair-dyeing composition of claim 1 wherein the alkalizing agent consists of the mixture.

* * * * *